United States Patent
Choi

(10) Patent No.: US 12,402,629 B2
(45) Date of Patent: Sep. 2, 2025

(54) ASPERGILLUS TERREUS STRAIN AND COMPOSITION FOR CONTROLLING BACTERIAL PLANT DISEASES USING STRAIN OR CULTURE FILTRATE THEREOF

(71) Applicant: Andong National University Industry-Academic Cooperation Foundation, Andong-si (KR)

(72) Inventor: Hyong Woo Choi, Andong-si (KR)

(73) Assignee: Andong National University Industry-Academic Cooperation Foundation, Andong-si (KR)

(*) Notice: Subject to any disclaimer, the term of this patent is extended or adjusted under 35 U.S.C. 154(b) by 167 days.

(21) Appl. No.: 18/161,008

(22) Filed: Jan. 27, 2023

(65) Prior Publication Data

US 2023/0240304 A1 Aug. 3, 2023

(30) Foreign Application Priority Data

Jan. 28, 2022 (KR) .......................... 10-2022-0013158

(51) Int. Cl.
*A01N 63/34* (2020.01)
*A01P 1/00* (2006.01)
*C12N 1/14* (2006.01)
*C12R 1/66* (2006.01)

(52) U.S. Cl.
CPC .............. *A01N 63/34* (2020.01); *A01P 1/00* (2021.08); *C12N 1/145* (2021.05); *C12R 2001/66* (2021.05)

(58) Field of Classification Search
CPC ........... A01N 63/34; C12N 1/145; A01P 1/00; C12R 2001/66

USPC ..................................................... 424/195.15
See application file for complete search history.

(56) References Cited

FOREIGN PATENT DOCUMENTS

| KR | 10-1524651 B1 | 6/2015 |
| KR | 10-1953835 B1 | 3/2019 |
| KR | 10-2240972 B1 | 4/2021 |

OTHER PUBLICATIONS

Choi et al., Biocontrol Activity of Aspergillus terreus ANU-301 against Two Distinct Plant Diseases, Tomato Fusarium Wilt and Potato Soft Rot, Plant Pathol. J., vol. 38, No. 1 (2022), pp. 33-45.*
Tsror et al., "Assessment of recent outbreaks of *Dickeya* sp. (syn. Erwinia chrysanthemi) slow wilt in potato crops in Israel", European Journal of Plant Pathology, 2009, 123(3): 311-320.
Slawiak et al., "Biochemical and genetical analysis reveal a new clade of biovar 3 *Dickeya* spp. strains isolated from potato in Europe", European Journal of Plant Pathology, 2009, 125(2): 245-261.

* cited by examiner

*Primary Examiner* — Jennifer M.H. Tichy
(74) *Attorney, Agent, or Firm* — You & IP, LLC

(57) ABSTRACT

Disclosed are *Aspergillus terreus* ANU-301 strain (Accession Number: KACC49929), and ANU-301 strain (Accession Number: KACC49929) and a composition for controlling bacterial plant diseases using the culture filtrate. Since the strain or culture filtrate, according to the present disclosure, enhances the stress resistance of plants, it enables sustainable agriculture to eliminate or minimize the use of chemical pesticides.

6 Claims, 4 Drawing Sheets

Specification includes a Sequence Listing.

ASPERGILLUS TERREUS STRAIN AND COMPOSITION FOR CONTROLLING BACTERIAL PLANT DISEASES USING STRAIN OR CULTURE FILTRATE THEREOF

REFERENCE TO A FOREIGN PRIORITY

The present application claims priority to Korean Patent Application No. 10-2022-0013158, filed Jan. 28, 2022, the entire contents of which is incorporated herein for all purposes by this reference.

REFERENCE TO AN ELECTRONIC SEQUENCE LISTING

The contents of the electronic sequence listing (PANY-110-Sequence_List_US.xml; Size: 2,640 bytes; and Date of Creation: Jan. 27, 2023) is herein incorporated by reference in its entirety.

BACKGROUND OF THE INVENTION

1. Field of the Invention

The present disclosure relates to a composition for controlling bacterial plant diseases using a novel microorganism and a culture filtrate thereof. More particularly, the present disclosure relates to a composition for controlling bacterial plant diseases using a novel *Aspergillus terreus* strain and a culture filtrate thereof.

2. Description of the Related Art

In modern agriculture, the development of biological control agents that can replace or supplement chemical pesticides has been required due to problems such as environmental pollution and residual pesticides caused by the continuous use of chemical pesticides. The development of biological control agents using various microorganisms existing in nature is essential for sustainable agriculture by reducing the use of chemical pesticides.

Korean Patent No. 10-1524651 (Composition for controlling bacterial plant diseases containing *Streptomyces griseus* S4-7' strain or its culture medium as an active ingredient), Korean Patent No. 10-2240972 (Composition for controlling bacterial plant disease containing Arborvitae extract or its fraction as an active ingredient and method for controlling bacterial plant disease using the composition), and Korean Patent No. 10-1953835 (*Aspergillus terreus* strains for enhancing plant disease resistance and uses thereof) are disclosed for sustainable biological control agents.

Potato soft rot caused by Dikeya species has been reported to cause economic losses related to potatoes in Korea and Europe (Tsror et al., "Assessment of recent outbreaks of *Dickeya* sp. (syn. *Erwinia chrysanthemi*) slow wilt in potato crops in Israel", European Journal of Plant Pathology, 2009, 123(3): 311-320; Slawiak et al., "Biochemical and genetical analysis reveal a new clade of biovar 3 *Dickeya* spp. strains isolated from potato in Europe", European Journal of Plant Pathology, 2009, 125(2): 245-261). As a way to reduce the damage caused by *Dickeya* species in potatoes, efforts have been made to suppress infection through tubers, but the effect is known to be insignificant. In particular, it is not possible to kill infiltrated pathogens by treatment with systemic bactericides.

SUMMARY OF THE INVENTION

An objective of the present disclosure is to provide a novel *Aspergillus terreus* ANU-301 strain (accession number: KACC93378P, which is deposited at Korean Agricultural Culture Collection (KACC). The KACC acquired the status of International Depositary Authority under the Budapest Treaty on May 1, 2015 (see Budapest Notification No. 307) and is located at 166 Nongsaengmyeong-ro, Iseomyeon, Wanju-gun, Jeollabuk-do, Republic of Korea 55365) that can be prescribed in the pre-growth stage and a composition for controlling bacterial plant diseases using the culture filtrate.

In addition, an objective of the present disclosure is to provide a method for eliminating or minimizing the use of pesticides by enhancing the stress resistance of plants and enabling sustainable agriculture.

The effects and advantages that can be achieved by the present disclosure are not limited to the ones mentioned above, and other effects and advantages which are not mentioned above but can be achieved by the present disclosure can be clearly understood by those skilled in the art from the following description.

According to an aspect of the present disclosure, in order to solve the above technical problem, the *Aspergillus terreus* ANU-301 strain (Accession No.: KACC93378P) is provided.

Here, the strain, according to the present disclosure, includes the nucleotide sequence internal transcribed spacer (ITS) represented by SEQ ID NO: 1.

Here, the present disclosure provides a composition for controlling bacterial plant diseases, including the *Aspergillus terreus* ANU-301 strain (Accession No.: KACC93378P), culture filtrate of the strain, or both as an active ingredient.

Here, the bacterial plant disease may be potato soft rot.

Here, the bacterial plant disease may be caused by *Dickeya chrysanthemi*

According to another aspect of the present disclosure, a composition for enhancing stress resistance of a plant comprising *Aspergillus terreus* ANU-301 strain (Accession Number: KACC93378P) or a culture filtrate of the strain as an active ingredient is provided.

According to another aspect of the present disclosure, provided is a method for enhancing the stress resistance of a plant, including a step of treating at least one selected from the group consisting of *Aspergillus terreus* ANU-301 strain (accession number: KACC93378P), a culture filtrate of the strain, a composition containing the strain, and a composition containing the culture filtrate of the strain to the plants, areas around the plants, or both.

Here, the resistance enhancement method may be provided by treating at least one selected from the group consisting of seeds, roots, stems, leaves, and whole plants of the plant.

According to the present disclosure, a novel *Aspergillus terreus* ANU-301 strain (accession number: KACC93378P) that can be prescribed in the pre-growth stage, and a composition for controlling bacterial plant diseases using the culture filtrate may be provided.

According to another embodiment of the present disclosure, since the stress resistance of plants is enhanced, the use of chemical pesticides may be eliminated or minimized by enabling sustainable agriculture.

The effects and advantages that can be achieved by the present disclosure are not limited to the ones mentioned above, and other effects and advantages which are not mentioned above but can be achieved by the present disclosure can be clearly understood by those skilled in the art from the following description.

DESCRIPTION OF THE PREFERRED EMBODIMENTS

Figure 1:
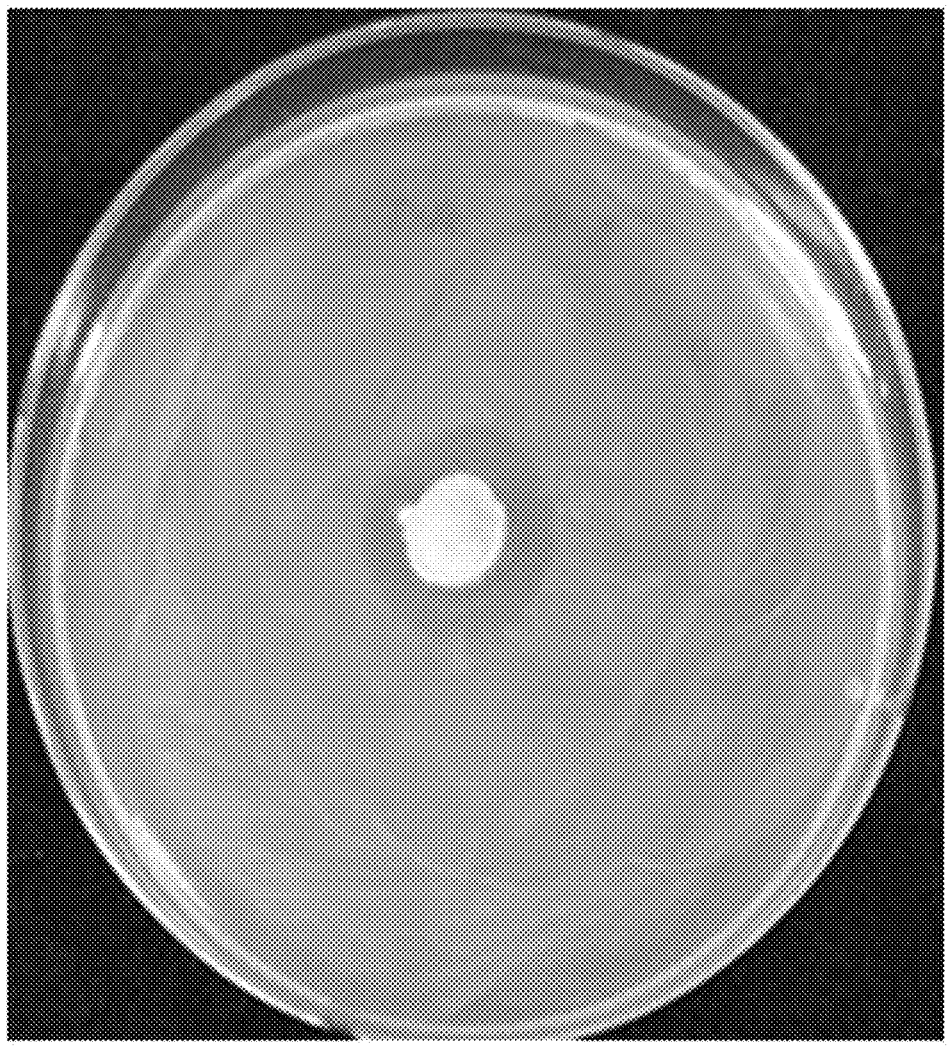
FIG. 1 is a diagram showing that the ANU-301 strain has an activity to inhibit the growth of bacterial phytopathogenic bacteria (*Dickeya chrysanthemi*) on a culture medium.

Purposes and effects of the present disclosure and technical configurations for achieving them will become clear with reference to the embodiments described below in detail, together with the accompanying drawings. In describing the present disclosure, well-known functions or constructions will not be described in detail when it is determined that they may obscure the gist of the present disclosure. In addition, the terms to be described later are terms defined in consideration of donation in the present disclosure, which may vary according to the intention or custom of the user or operator.

However, the present disclosure is not limited to the embodiments disclosed below and may be implemented in a variety of different forms. However, the present embodiments are provided to complete the disclosure of the present disclosure and to completely inform the scope of the present disclosure to those skilled in the art, and the present disclosure is only defined by the scope of the claims. Therefore, the definition should be made based on the content throughout this specification.

Hereinafter, embodiments of the present disclosure will be described in detail.

In this specification, "plant" refers to any living organism belonging to the plant family (i.e., any genus/species in the plant family), such as trees, herbs, shrubs, pastures, vines, ferns, mosses, and green algae, but is not limited thereto. Accordingly, representative plants to which the composition may be applied include, but are not limited to, brassica, bulbous vegetables, grains, citrus, cotton, gourds, fruit vegetables, leaf vegetables, legumes, oilseed crops, peanuts, pomes, root vegetables, tuber vegetables, corm vegetables, stone fruits, tobacco, strawberries, and various ornamental plants. Plants herein may be potatoes, peppers, tomatoes, or paprika.

In the present specification, "culture medium" or "culture filtrate" is a result obtained by inoculating a strain into a medium and culturing for a certain period of time, including the culture medium itself in which the strain, according to the present disclosure, is cultured in a suitable liquid medium, a filtrate obtained by removing the strain by filtering or centrifuging the culture solution (filtrate or centrifuged supernatant), a cell lysate obtained by sonicating the culture medium or treating the culture medium with lysozyme, and concentrate obtained by concentrating the culture medium, filtrate, and lysate, etc., but not limited thereto. In addition, the probiotic or antibacterial composition may contain a culture such as a solid culture medium or a dried product or extract of the culture medium, but is not limited thereto and may further include a suitable excipient or carrier.

The composition of the present disclosure may be prepared in the form of a liquid fertilizer, and a thickener may be added thereto to be used in the form of powder or may be formulated to be granulated. However, the formulation is not particularly limited thereto.

The composition for enhancing plant stress resistance of the present disclosure can enhance plant resistance to any one or more stresses selected from the group consisting of moisture, temperature, salt, pH, nutrition, and pathogens, and inhibition of disease development, and growth.

In the present specification, "stress" may be biological, non-biological, or biological stress on plants, and specifically, the non-biological stress may be dry, high temperature, low temperature, high salt, or nutrient deficiency. The term "non-biological stress" is used in its usual sense as a negative effect of non-biological factors on living organisms in a particular environment and thus means the negative effect of non-biological factors on plants in a particular environment. While biological stress includes living disturbances such as fungi or harmful insects, non-biological stress factors including temperature, dry soil, osmotic stress, drought, salt, or nutrient deficiency, may be spontaneous or man-made, all of which can cause harm to plants in the affected area. For example, salt stress can include increased salt concentrations or drought. A nutrient deficiency can be a lack of soil nutrients, such as potassium, phosphate, or iron, in the soil area around the plant. Increased stress resistance to (soil) nutrients, such as phosphate deficiency, can be provided by improved solubilization of nutrients that are lacking in the soil.

The term "resistance (or tolerance) to salt" is used herein in its usual sense to refer to the resistance (tolerance) of a plant to salt concentrations. Therefore, "increasing the salt tolerance or resistance of a plant" means that a plant's ability to withstand or tolerate salt concentrations (in its environment, such as soil or water) is usually increased or improved when exposed to plants at salt concentrations higher than physiologically acceptable salt concentrations.

The term "water resistance (or tolerance)" or "dry resistance (or tolerance)" is also used herein in its usual sense for the plant's ability to avoid stress and consequences by maintaining desirable moisture balance and expansion even when exposed to dry conditions. Accordingly, "increasing moisture (or dry) resistance" of a plant means increasing or improving the plant's ability to maintain desirable moisture balance and expansion when exposed to drought conditions where the plant is not regularly supplied with the amount of water required to maintain moisture balance and expansion.

The term "plant pathogen" means a pathogen that invades plants and causes loss and damage to the leaves, stems, roots, or fruits of plants, including, such as fungi, bacteria, viruses, and phytoplasma.

The term "plant pathogen resistance" or "bacterial resistance" usually means the ability to improve plant growth away from infection and growth of pathogens, and enhancing resistance to these pathogens includes the meaning of control, sterilization, and insect control used in the field.

The composition for enhancing plant stress resistance, according to the present disclosure, may enhance plant resistance, disease occurrence inhibition, and growth against pathogen stress that causes at least one bacterial plant disease selected from the group consisting of *Ralstonia solanacearum* and *Phytophthora capsici*.

The composition for enhancing stress resistance of plants of the present disclosure may enhance resistance, disease occurrence inhibition, and growth of at least one plant selected from the group consisting of trees, herbs, shrubs, pastures, vines, ferns, mosses, green algae, monocotyledonous plants, and dicotyledonous plants.

The present disclosure exhibits enhancement or promotion of plant growth through enhancement of plant stress resistance. In the above, "plant growth" means the germination of plants, the differentiation, flowering or development of each organ (root, stem, leaf, fruit, etc.), the improvement of size and weight, and the improvement of quantity.

The composition for enhancing plant stress resistance of the present disclosure may further include any other component used to enhance plant stress resistance or promote growth in the strain of the present disclosure, the strain culture solution, or a mixture thereof. For example, at least one selected from the group consisting of a plant growth regulator, plant growth stimulant, and plant nutrient may be further included.

The plant growth regulator, plant growth stimulant, or plant nutrient may be a chemical substance or another strain of bacteria and may be an herbicide, fungicide, pesticide, fertilizer, or any combination thereof.

The composition for promoting plant growth of the present disclosure may include other beneficial microorganisms, microbial active substances, organic fertilizers, and chemical fertilizers. Other beneficial microorganisms may include *Bacillus* spp., *Azotobacter* spp., *Trichoderma* spp., and *Saccharomyces* spp., which are known to promote plant growth.

The microbial activate substance may include enzyme precursors, microbial metabolites, organic acids, carbohydrates, enzymes, and/or trace elements. For example, microbial activate substances may include processed enzyme products such as yeast autolysates, humic materials, seaweed extracts, starch, amino acids, and trace elements such as zinc, iron, copper, manganese, bromine, and molybdenum.

Other beneficial microorganisms, microbial activate substances, and organic fertilizers may be the same as described above. Chemical fertilizers may contain a variety of chemicals that can provide nitrogen, phosphorus, and potassium nutrients to support plant growth. For example, chemical fertilizers may include urea, calcium phosphate, potassium phosphate, and mixed nitrogen-phosphate-potassium (N—P—K) fertilizers. Chemical fertilizers may also include other materials known in the art.

The present disclosure provides a method for enhancing the stress resistance of a plant, including the step of treating at least one selected from a group consisting of *Aspergillus terreus* ANU-301 strain (Accession No.: KACC93378P), a culture solution of the strain, a composition containing a strain, and a composition containing a culture solution of the strain to the plant, the area around the plant, or both.

The plant part applied to the embodiment of the present disclosure is not limited. Therefore, the whole plant as well as parts of the plant, such as seeds, shoots, stems, roots, leaves, and fruits, all of these as well as parts thereof are included.

An embodiment of the present disclosure may be performed by immersing or drenching, i.e., spraying, the strain, a culture solution in which the strain is cultured, and a composition using the strain to a seed or plant. In the case of the immersion method, the culture solution and the formulation may be drenched in the soil around the plant, or the seed may be immersed in the culture solution and the composition for shaking inoculation.

The surrounding area applied according to the embodiment of the present disclosure means a range in which the composition of the present disclosure can exert an effect and includes both ground and underground areas. For example, it may be an area within about 2 m, within about 1 m, within about 70 cm, within about 50 cm, within about 25 cm, within about 10 cm, or within about 5 cm around a plant, plant part, or fruit.

A method according to an embodiment of the present disclosure includes continuously applying a composition comprising *Aspergillus terreus* ANU-301 strain at any point during the life cycle of the plant, during one or more phases of the life cycle of the plant, or at regular intervals in the life cycle of the plant or throughout the life cycle of a plant. Accordingly, the composition may be applied as needed. The composition may be applied to the plant, for example, during growth, before and/or during flowering and/or before and/or during seed development. In one example, the composition may be applied before, during and/or immediately after the plant is transplanted from one location to another, for example, from a greenhouse or hotbed to a field. In another example, each composition may be applied to the plant multiple times at desired interval periods.

The method for enhancing plant stress resistance of the present disclosure may enhance plant resistance to any one or more stresses selected from the group consisting of moisture, temperature, salt, pH, nutrition, and pathogens, inhibition of disease development and growth.

The method for enhancing plant stress resistance, according to the present disclosure, may enhance plant resistance to pathogen stress causing one or more bacterial plant diseases selected from the group consisting of green blight and late blight, inhibiting disease occurrence, and enhancing growth. Details of the pathogen are as described above.

The method for enhancing stress resistance of the plants of the present disclosure may enhance resistance, disease occurrence inhibition, and growth of at least one plant selected from the group consisting of trees, herbs, shrubs, pastures, vines, ferns, mosses, green algae, terminal plants, and dicotyledonous plants.

The present disclosure provides a method for promoting plant growth, including the step of treating at least one selected from a group consisting of *Aspergillus terreus* ANU-301 strain (Accession No.: KACC93378P), a culture solution of the strain, a composition containing a strain, and a composition containing a culture solution of the strain to the plant, the area around the plant, or both.

The method for promoting plant growth of the present disclosure may promote the growth of one or more plants selected from the group consisting of trees, herbs, shrubs, grasses, vines, ferns, moss, green algae, monocotyledonous plants, and dicotyledonous plants.

For the present disclosure, the soil in the farm located in Andong University (1375 Gyeongdong-ro, Andong-city, Gyeongsangbuk-do) was collected to separate various bacteria present in the soil, and among them, *Aspergillus terreus* ANU-301 strain, which shows an antibacterial effect against *Dickeya chrysanthemi*, which is a bacterial phytopathogenic bacterium, was newly discovered.

In order to observe the antagonistic effect of the *Aspergillus terreus* ANU-301 strain of the present disclosure on

*Dickeya chrysanthemi* (potato soft rot), PDA medium (Potato dextrose agar medium: potato infusion 4.0 g, Dextrose 20.0 g & Agar 15.0 g/1 L) were smeared with *Dickeya chrysanthemi* bacteria, and ANU-301 strain was simultaneously cultured in the center of the medium. It was found that the bacteria *Dickeya chrysanthemi* did not grow in the vicinity of the ANU-301 strain(FIG. 1).

This indicates that the ANU-301 strain has a direct antagonistic effect on *Dickeya chrysanthemi* bacteria.

Figure 2:
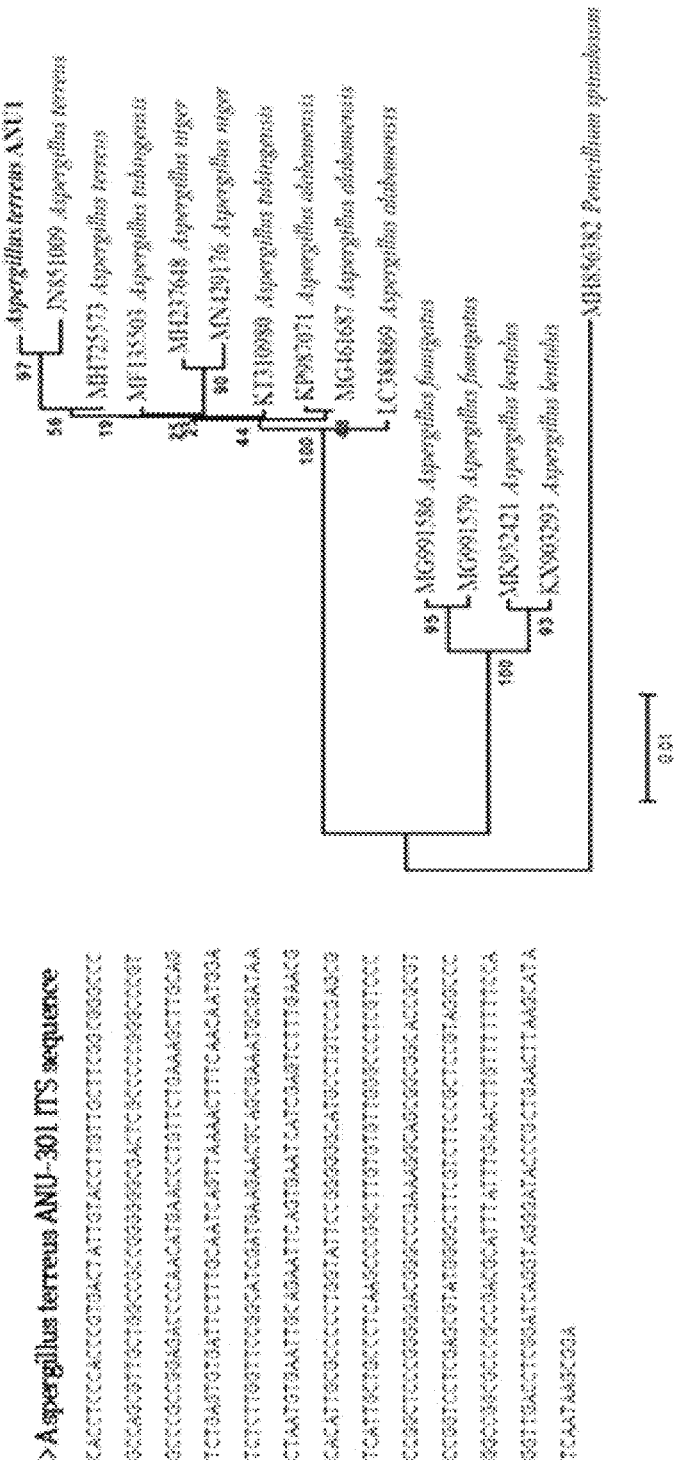
FIG. 2 is a diagram showing that the ANU-301 strain belongs to *Aspergillus terreus* molecularly phylogenetically through internal transcribed spacer (ITS) sequencing.

The *Aspergillus terreus* ANU-301 strain of the present disclosure was identified through internal transcribed spacer (ITS) sequencing and phylogenetic analysis (FIG. 2). The *Aspergillus terreus* ANU-301 strain of the present disclosure includes an internal transcribed spacer (ITS) of the nucleotide sequence represented by SEQ ID NO: 1.

Figure 3:
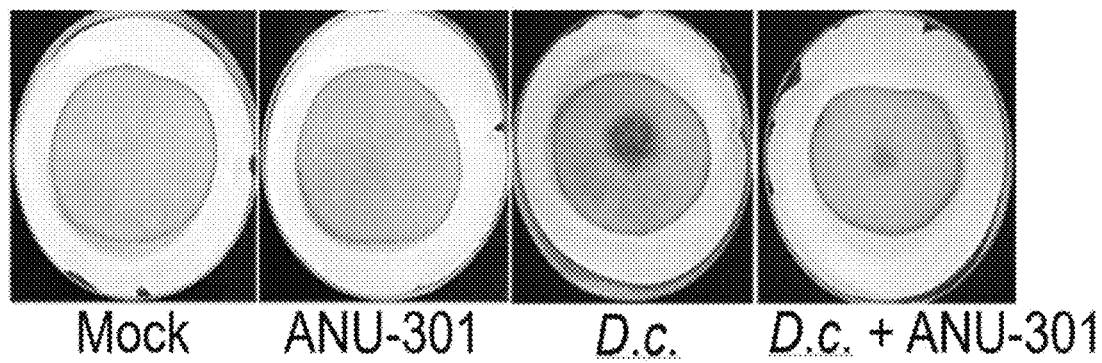
FIG. 3 is a diagram showing that the ANU-301 strain is effective in controlling potato soft rot caused by *Dickeya chrysanthemi* in potato plants.

In order to test whether the culture filtrate of the *Aspergillus terreus* ANU-301 strain of the present disclosure has a control effect on potato soft rot caused by *Dickeya chrysanthemi* bacteria, a pathogen inoculation experiment was performed (FIG. 3).

When potato plants were treated with culture filtrate of *Aspergillus terreus* ANU-301 strain, no change was observed in potato plants as in Mock (non-inoculated experimental group), demonstrating that there is no harmful effect of culture filtrate. In potato plants inoculated with *Dickeya chrysanthemi* bacteria (D.c.), browning progressed at the inoculation site, and symptoms of soft rot disease were confirmed. However, in potato plants treated with the culture filtrate of *Dickeya chrysanthemi* bacteria (D.c.) and ANU-301 strain at the same time, soft rot symptoms were suppressed, confirming that there was a direct disease control effect.

Figure 4:
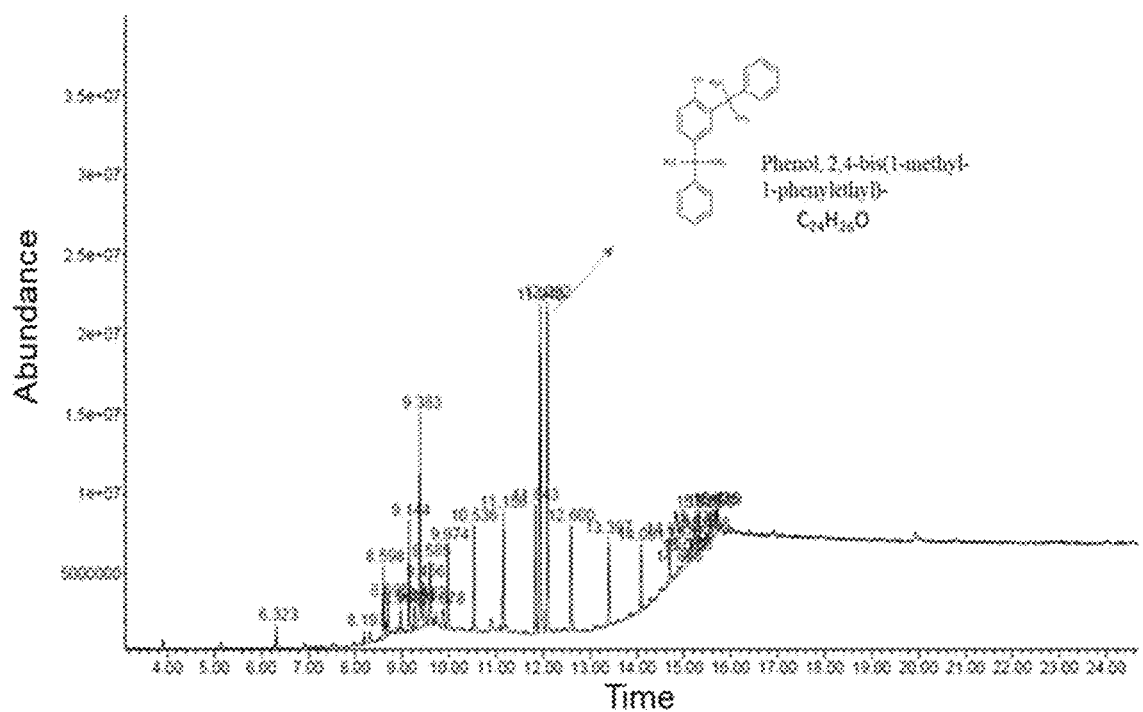
FIG. 4 is a diagram showing that 2,4-bis(1-methyl-1-phenylethyl)-phenol (MPP) was detected as the main component as a result of gas chromatography-mass spectrometer (GC/MS/MS) analysis of ANU-301 strain culture extract.

In order to analyze substances exhibiting antibacterial activity in the culture filtrate of *Aspergillus terreus* ANU-301 strain of the present disclosure, gas chromatography mass spectrometry (GC/MS/MS) analysis was performed (FIG. 4). As a result, a substance called 2,4-bis(1-methyl-1-phenylethyl)-phenol (MPP) was detected as the main component.

Figure 5:
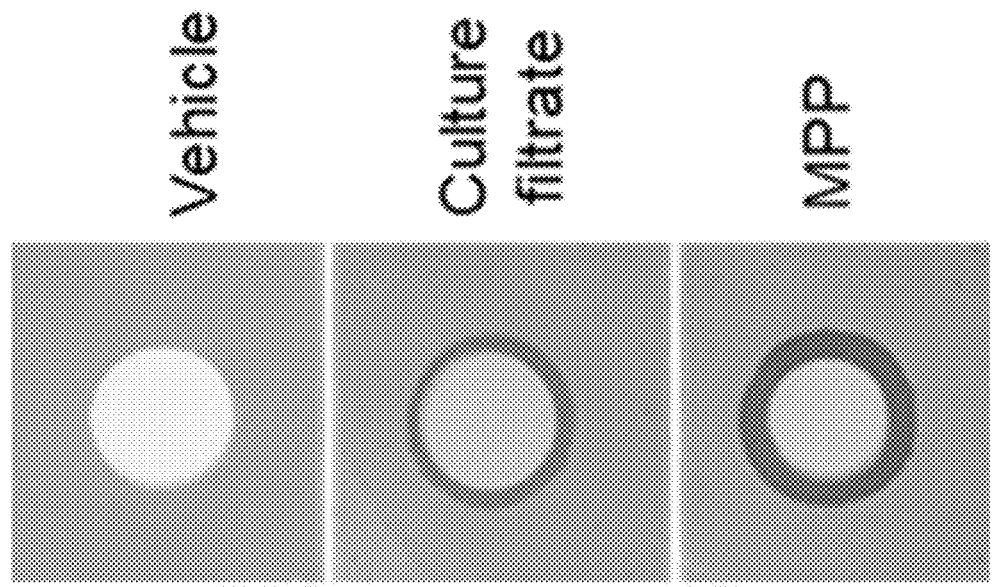
FIG. 5 is a diagram showing that the ANU-301 strain culture extract and MPP material have an activity to inhibit the growth of bacterial phytopathogenic potato soft rot on the medium.

Disc diffusion assay to determine whether the 2,4-bis(1-methyl-1-phenylethyl)-phenol (B) substance present in the culture filtrate of *Aspergillus terreus* ANU-301 strain exhibits actual antibacterial activity (disc diffusion assay) was performed (FIG. 5).

To this end, the NA medium (Nutrient agar medium: peptone 5 g, beef extract 1.5 g, yeast extract 1.5 g, NaCl 5 g & agar 15 g/1 L) was smeared with *Dickeya chrysanthemi* bacteria. After placing a paper filter disk in the center of the medium, 10 μL of culture extract and 400 ppm of MPP were wetted therein, respectively, and the result of culturing the bacteria was observed. As a result of the observation, it was found that bacteria did not grow, and a clear zone was formed around the culture filtrate and MPP material treated. This indicates that the culture filtrate of the *Aspergillus terreus* ANU-301 strain and the MPP component present in the culture filtrate shows a direct antibacterial effect.

Figure 6:
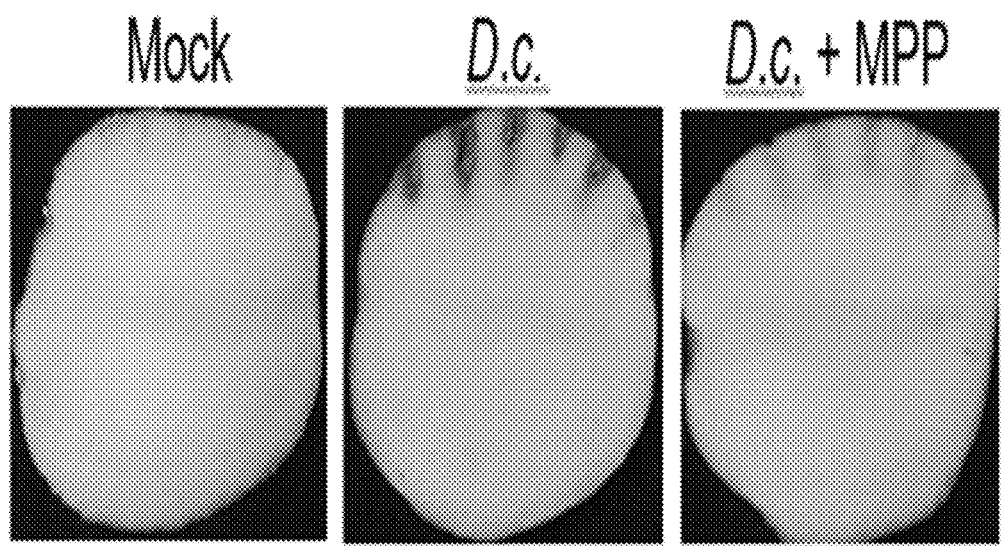
FIG. 6 is a diagram showing that the MPP material is effective in controlling potato soft rot caused by *Dickeya chrysanthemi* in potato plants.

A pathogen inoculation experiment was conducted to test whether the MPP component present in the culture filtrate of the *Aspergillus terreus* ANU-301 strain of the present disclosure is effective in controlling potato soft rot disease caused by *Dickeya chrysanthemi* bacteria (FIG. 6). In potato plants inoculated with *Dickeya chrysanthemi* bacteria (D.c.), browning progressed at the inoculation site, and symptoms of soft rot disease were confirmed. However, in potato plants treated with *Dickeya chrysanthemi* bacteria (D.c.) and MPP at the same time, soft rot symptoms were suppressed, confirming that MPP material has a direct disease control effect on potato soft rot. Hereinafter, the present disclosure will be described in more detail with reference to Examples. However, these examples are presented merely to describe the present disclosure in more detail, and the scope of the present disclosure is not limited to these examples.

Example 1: Screening and Identification of ANU-301 Strain

Total gDNA was isolated using a gDNA isolation kit to classify and identify the ANU-301 strain. Then, the ITS portion was amplified through polymerase chain reaction (PCR) using ITS1 (5'-TCC GTA GGT GAA CCT GCG G3') and ITS4 (5'-TCC TCC GCT TAT TGA TAT GC3') primers.

The PCR was treated under the conditions of once for 5 minutes at 95° C., 30 seconds at 94° C., 10 seconds at 56° C., and 40 seconds at 72° C., and were repeated 33 times and then maintained at 72° C. for 10 minutes. After analyzing the nucleotide sequence of the amplified PCR portion, species with similar nucleotide sequences were identified using the BLAST network service at the National Center for Biotechnology Information (NCBI).

As a result of phylogenetic analysis, the ANU-301 strain was found to have 100% similarity with *Aspergillus terreus* in the ITS nucleotide sequence (552 bp), confirming that it was an *Aspergillus terreus* species. However, it is not distinguished whether it is the same as *Aspergillus terreus* isolate F8172, *Aspergillus terreus* isolate F8159, or *Aspergillus terreus* isolate C23-3, which are variants of *Aspergillus terreus* (FIG. 2).

Example 2: Evaluation of Potato Soft Rot Inhibitory Effect of ANU-301 Strain Culture Filtrate In order to evaluate the effect of the ANU-301 strain culture filtrate on potato soft rot inhibition, the culture filtrate was prepared as follows.

The ANU-301 strain was inoculated into sterilized potato dextrose broth (PDB) and cultured at 25° C. for 5 days.

In order to remove the fungi and spores of ANU-301 strains, the supernatant was collected through centrifugation at 13,000 rpm for 10 minutes and sterilized through a filter (pore size=0.22 μm).

Potatoes were immersed in 1% NaOCl for 5 minutes and 70% ethanol for 5 minutes to sterilize the surface and washed three times with sterilized distilled water.

In potatoes inoculated with bacterial suspension ($2 \times 10^6$ cfu/ml) of potato soft rot (D.c.), symptoms of soft rot disease were confirmed, but symptoms were not observed in the untreated group (FIG. 3, Mock) and potatoes treated with the culture filtrate of the ANU-301 strain diluted 1/100.

Importantly, potatoes treated with bacterial suspension ($2 \times 10^6$ cfu/ml) of potato soft rot (D.c.) and culture filtrate of 1/100 diluted ANU-301 strain showed a disease-inhibiting effect (FIG. 3, D.c.+ANU-301), and it was confirmed that the culture filtrate of ANU-301 strain could suppress potato soft rot disease effectively.

Example 3: Potato Soft Rot Inhibitory Effect of 2,4-bis(1-methyl-1-phenylethyl)-phenol (MPP), a Major Component of ANU-301 Strain Culture Filtrate Gas chromatography-mass spectrometry (GC/MS/MS) analysis was performed to investigate components exhibiting antibacterial activity against potato soft rot in the culture filtrate of ANU-301 strain (FIG. 4). As a result, a substance called 2,4-bis(1-methyl-1-phenylethyl)-phenol (MPP) was detected as the main component.

FIG. 5 is a diagram showing that the ANU-301 strain has an activity to inhibit the growth of bacterial phytopathogenic bacteria (*Dickeya chrysanthemi*: potato soft rot) on a culture medium.

As a result of confirming the inhibitory effect of MPP on potato soft rot, potatoes simultaneously treated with a bacterial suspension ($2 \times 10^6$ cfu/ml) of potato soft rot (D.c.) and 400 ppm MPP (FIG. 6, D.c.+MPP) showed a disease inhibitory effect compared to potatoes (FIG. 6, D.c.) treated only with a bacterial suspension ($2 \times 10^6$ cfu/ml) of potato soft rot bacteria. It was confirmed that MPP, a major component of the culture filtrate of ANU-301 strain, could effectively inhibit potato soft rot.

The present specification and drawing disclose a preferred embodiment of the present disclosure, and although specific terms are used, they are used in a general sense to easily explain the technical contents of the present disclosure and help understanding of the present disclosure, not to limit the scope of the present disclosure. In addition to the embodiments disclosed herein, it is obvious to those skilled in the art that other modified examples based on the technical idea of the present disclosure may be implemented.

at least one plant nutrient selected from the group consisting of urea, calcium phosphate, potassium phosphate, and nitrogen-phosphate-potassium (N—P—K) fertilizers; and at least one beneficial microorganism selected from the group consisting of *Bacillus* spp., *Azotobacter* spp., *Trichoderma* spp., and *Saccharomyces* spp.

2. The composition of claim 1, wherein the bacterial plant disease is potato soft rot.

3. The composition of claim 2, wherein the bacterial plant disease is caused by *Dickeya chrysanthemi*.

4. A composition for enhancing stress resistance of a plant, the composition comprising:

2,4-bis(1-methyl-1-phenylethyl)-phenol (MPP) contained in a culture filtrate of *Aspergillus terreus* ANU-301 strain (Accession No.: KACC93378P) as an active ingredient, wherein the MPP is present at a concentration of 400 ppm;

at least one plant nutrient selected from the group consisting of urea, calcium phosphate, potassium phosphate, and nitrogen-phosphate-potassium (N—P—K) fertilizers; and at least one beneficial microorganism selected from the group consisting of *Bacillus* spp., *Azotobacter* spp., *Trichoderma* spp., and *Saccharomyces* spp.

5. A method for enhancing stress resistance of a plant, the method comprising treating a plant, an area around a plant, or both with a composition comprising:

2,4-bis(1-methyl-1-phenylethyl)-phenol (MPP) contained in a culture filtrate of *Aspergillus terreus* ANU-301 strain (Accession No.: KACC93378P) as an active ingredient, wherein the MPP is present at a concentration of 400 ppm;

What is claimed is:

1. A composition for controlling bacterial plant diseases, the composition comprising:

2,4-bis(1-methyl-1-phenylethyl)-phenol (MPP) contained in a culture filtrate of *Aspergillus terreus* ANU-301 strain (Accession No.: KACC93378P) as an active ingredient, wherein the MPP is present at a concentration of 400 ppm;

at least one plant nutrient selected from the group consisting of urea, calcium phosphate, potassium phosphate, and nitrogen-phosphate-potassium (N—P—K) fertilizers; and at least one beneficial microorganism selected from the group consisting of *Bacillus* spp., *Azotobacter* spp., *Trichoderma* spp., and *Saccharomyces* spp.

6. The method of claim 5, wherein the treatment is performed on at least one selected from the group consisting of seeds, roots, stems, leaves, and whole plants of the plant.

* * * * *

SEQUENCE LISTING

```
Sequence total quantity: 1
SEQ ID NO: 1            moltype = DNA   length = 552
FEATURE                 Location/Qualifiers
source                  1..552
                        mol_type = genomic DNA
                        organism = Aspergillus terreus
SEQUENCE: 1
cacctcccac ccgtgactat tgtaccttgt tgcttcggcg ggcccgccag cgttgctggc   60
cgccgggggg cgactcgccc ccgggcccgt gcccgccgga gaccccaaca tgaaccctgt  120
tctgaaagct tgcagtctga gtgtgattct ttgcaatcag ttaaaacttt caacaatgga  180
tctcttggtt ccggcatcga tgaagaacgc agcgaaatgc gataactaat gtgaattgca  240
gaattcagtg aatcatcgag tctttgaacg cacattgcgc ccctggtat tccgggggc   300
atgcctgtcc gagcgtcatt gctgccctca agcccggctt gtgtgttggg ccctcgtccc  360
ccggctcccg ggggacgggc ccgaaaggca gcggcgggca gcgtccggt cctcgacgt   420
atgggcttc gtcttccgct ccgtaggccc ggccggcgcc cgccgacgca tttatttgca  480
acttgttttt ttccaggttg acctcggatc aggtagggat acccgctgaa cttaagcata  540
tcaataagcg ga                                                     552
```